United States Patent [19]

Coves et al.

[11] Patent Number: 5,108,908
[45] Date of Patent: Apr. 28, 1992

[54] PROCESS FOR THE TREATMENT OF PROTEINIC SOLUTIONS CONTAINING PIGMENTS SUCH AS HEMINIC GROUPS OR CHLOROPHYLLS IN VIEW OF THEIR DECOLORIZATION AND PRODUCTS THUS OBTAINED

[75] Inventors: Jacques Coves, Grenoble; Jean-Louis Tayot, La Tour de Salvagny, both of France

[73] Assignees: Imedex, Lyon; Dibevial, Corbas, both of France

[21] Appl. No.: 582,643

[22] Filed: Sep. 14, 1990

[30] Foreign Application Priority Data

Aug. 2, 1988 [FR] France ................................ 88 10405
Sep. 14, 1989 [EP] European Pat. Off. ......... 89402513.9

[51] Int. Cl.$^5$ ...................... C12P 21/06; A23L 1/31; A23J 3/30
[52] U.S. Cl. ..................................... 435/68.1; 435/2; 435/800; 426/647; 514/6; 530/414; 530/420
[58] Field of Search .................... 435/68.1, 800, 2; 530/414, 420, ; 426/647; 514/6

[56] References Cited

U.S. PATENT DOCUMENTS

| | | | |
|---|---|---|---|
| 3,928,630 | 12/1975 | Perini | 435/68.1 |
| 4,262,022 | 4/1981 | Hald-Christensen | 426/647 |
| 4,411,915 | 10/1983 | Eriksson | 435/68.1 |
| 4,443,540 | 4/1984 | Chervan et al. | 435/68.1 |
| 4,473,589 | 9/1984 | Freeman et al. | 435/68.1 |
| 4,650,589 | 3/1987 | Piot et al. | 210/691 |
| 4,666,725 | 5/1987 | Yamashita et al. | 426/647 |
| 4,866,033 | 9/1989 | Jaeger | 435/68.1 |
| 4,986,998 | 1/1991 | Yoo et al. | 436/647 |

*Primary Examiner*—Lilling: Herbert J.
*Attorney, Agent, or Firm*—Larson & Taylor

[57] ABSTRACT

A process for pigments such as the treatment of proteinic solutions containing heminic groups or chlorophylls in view of their decolorization, and products thus obtained.

The proteinic solution is subjected in a first step, to a slight enzymatic hydrolysis, preferably with acid pH pepsin, and the partially hydrolyzed solution is then brought to a temperature above 60° C., at an acid pH between 2 and 4.

16 Claims, No Drawings

PROCESS FOR THE TREATMENT OF PROTEINIC SOLUTIONS CONTAINING PIGMENTS SUCH AS HEMINIC GROUPS OR CHLOROPHYLLS IN VIEW OF THEIR DECOLORIZATION AND PRODUCTS THUS OBTAINED

A process for the treatment of proteinic solutions containing pigments such as heminic groups or chlorophylls in view of their decolorization, and products thus obtained.

This invention relates to a process for treating proteinic solutions containing pigments, notably heminic groups or chlorophyll groups in view of their decolorization.

It also relates to decolored products obtained by application of said process.

Many highly interesting proteinic solutions, of animal or vegetal origin, contain pigments whose color is not stable through time. They cannot therefore be used as foodstuffs or pharmaceuticals because they often have defects in their taste or coloration.

The valorization of these proteinic solutions implies their decolorization, that is to say one must obtain on the one hand the white proteinic part (or derivatives of this proteinic part), and, on the other hand, pigments While the inventive process aims more particularly to decolorize substances obtained from animal blood such as hemoglobin, it may also be applied in an interesting manner for decolorizing vegetal proteinic solutions containing chlorophylls.

Hemoglobin may be found in the red blood cells (or erythrocytes) and is made up of four polypeptide (globin) chains which are each associated with a heminic group, the latter being made up of a tetrapyrrole ring containing an iron atom which may fix oxygen in a reversible manner. This heminic group is responsible for the red colour of the blood.

In like manner, a tetrapyrrol ring containing a magnesium atom is responsible for the green color of plants.

The presence of these pigments is most often undesirable in products obtained from the transformation of raw materials such as blood or vegetal substances. These pigments must therefore be eliminated so as to collect the proteins which contain them and are practically colorless in most cases.

Among the pigmented proteinic substances which may be made more valuable by decoloration, the blood, and more particularly the hemoglobin, is without doubt potentially the most interesting product and that which has been most studied.

Indeed, the 1980 French blood production amounted to about 200,000 tons, of which 80,000 were collected for the feeding of humans, cattle, or pharmacy, ... The 120,000 tons of blood which were not collected correspond to 20,000 tons of proteins having a high biological or technological value which are discarded as waste, which represents an enormous loss and an important source of pollution.

Generally, the blood of slaughterhouses is kept in a liquid state, as soon as the animals are bled, by adding a conventional anticoagulant such as sodium citrate or polyphosphates. A simple centrifugation step allows one to separate two fractions of different volume and composition. The light colorless fraction, which makes up 60 to 65% of the volume, is called plasma and is made good use of in the food industry (delicatessen and confectionery) and in the pharmaceutical industry (production of albumin for the most part). The remaining 35-40% make up the heavy fraction, which is called cruor, and which contains principally the red blood cells. This cruor is made up of about 30% proteins of which 90% are hemoglobin. Cruor obtains its intense red color precisely because of this high hemoglobin content, which hampers its application.

Several Patents have been filed for hemoglobin decoloration processes, but neither of them has proved profitable or efficient enough for technical application.

To separate the pigment from the protein (the heme of the globin) one must one the one hand cut the comparatively strong link which unites them and, on the other hand, isolate obtained compounds. This process is a delicate one, because the cleavage of the heme-globin link requires an acid pH (less than 4) and entails structural modifications such that the proteinic molecule precipitates if in concentrated solution. Moreover, given its hydrophobic nature, the pigment is insoluble in water and also precipitates.

Researchers have taken advantage of this hydrophobic property of the heme to extract it with the help of organic solvents made acid. This triggers simultaneously the cleavage of the heme-globin link, the solubilization of the pigment and the precipitation of the decolored protein. Regarding this point, one can refer to the work of TYBOR and al. Journal of Food Science 38, 4-6 (1973) which gives an example of heme extraction by acid acetone, or to the Patent PCT WO 81/02834 (LINDROOS) which describes an example of heme extraction by acid ethanol.

However, these processes entail prohibitive operating costs because of the important solvent volumes which are necessary to completely decolorize the proteins. Moreover, apart from safety problems, the solvent must be recirculated and the precipitated proteins are very difficult to dissolve again.

Another kind of operation comprises an acidification of an hemoglobin solution which is diluted by a factor 20-100 at a pH below 3, followed by contacting the obtained solution with carboxymethylcellulose (CMC), the pigment which is then freed by acidification being then adsorbed on CMC. Japanese Patent No. 55-008261 (SATO and HAYAKAWA) gives an example of a column adsorption process For their part, AUTIO and al., in Journal of Food Science (1980), 49, 859-862, present an ameliorated version of the same process comprising a batch adsorption.

Patent PCT/FR 82/00184 (ESPENAN) suggests another decoloration process based on the acid hydrolysis of a very diluted hemoglobin solution. The hydrolysis is carried out preferentially with sulfuric acid at a pH between 2 and 3, and the (reaction is accelerated by heating the acid solution at about 100° C. during 2-3 hours. One then obtains a decolorated supernatant by filtering or centrifugeing; this contains about 40% of the initial proteins. This process is interesting, being very simple, but it uses a lot of energy necessary to heat important volumes. Moreover, apart from the insufficient yields the majority of decolorized proteins obtained are insoluble at neutral pH because they precipitate in a pH range between 6 and 9, and concentrating them by centrifugation gives a light brown residue, a sign of incomplete decoloration.

Another kind of process comprises an enzymatic hydrolysis of hemoglobin from hemolysed cruor. An application is described by REGNIER in Revue Technique des Vétérinaires et de l'Alimentation (R.T.V.A.), 22, 23-35 (1983). Cruor is diluted to obtain a solution containing 8-19% proteins, and hydrolysis is carried out at a temperature of 52°-58° C. and at a pH of 8.5, which is automatically controlled during the 2 to 4 hours reaction by a pH stat. The enzyme used is NOVO Alcalase (subtilisine type). Separation between heme bearing peptides and decolorated peptides is carried by centrifugation or ultrafiltration. The decoloration of the obtained brown juice is carried out further by addition of activated carbon. The aim of this step is also to adsorb small peptides on the carbon, conferring a bitter taste and a nauseating smell. Eliminating the carbon by filtration allows one to obtain a yellow solution containing very small peptides which can only be concentrated by reverse osmosis and which have second rate technological properties.

Another process of this kind is described in French Patent FR-A-79 02940 which necessitates decolorizing step with activated carbon.

European Patent No. 0159231 describes another kind of enzymatic hydrolysis. The inventors hydrolyse a 5% hemoglobine solution with pepsine at 37° C. during 2-3 hours. pH is set to 2 with hydrochloric acid, and then automatically controlled at this value with a pH stat. The obtained highly colored centrifugation supernatant is then contacted with a column or in batch during several hours with an adsorbant chosen among magnesia or alumina A further centrifugation allows one to obtain a decolorized supernatant containing only 40-50% of initial proteins.

Aim of this invention is to obviate the above mentioned disadvantages by presenting a process for decolorizing proteinic solutions containing pigmented groups and which uses neither organic solvents, nor adsorbants, while allowing one to collect proteins with very high yields and to obtain an excellent decoloration.

One of the aims of this invention is to suggest a process for decolorizing an hemoglobin solution obtained by hemolysis of slaughterhouse cruor or of a green colored solution which is obtained by grinding plants, and which may be carried out in a particularly simple and economic manner.

Another aim of this invention is to suggest a process for decolorizing proteinic solutions containing heminic groups, in which one uses neither organic solvents nor pH regulators.

Another still different aim of the invention is to provide a protein-rich product or proteinic concentrate which is practically colorless and may be used for feeding animals as well as humans.

The process according to the invention is characterized in that it comprizes submitting in a first step, the proteinic solution to a slight enzymatic hydrolysis made at a suitable pH and temperature for the activity of the enzyme used, and then, in a second step, bringing the partially hydrolysed solution to a temperature above 60° C., and, preferably, lower than or equal to 80° C., at a pH between 2 and 5 and preferably 2-4, preferably with sulfuric acid.;

During the hydrolysis step, one can advantageously use as an enzyme pepsin at a pH between 2 and 4. One obtains good results with T pepsin 1,000 according to Codex 49 (obtainable from the Laboratoire Industriel de Biologie), which is generally used in a proportion between 0.1 and 0.5% in relation to the mass of proteins in solution. This enzyme may advantageously be solubilized in the same acid as that used to adjust the pH of the proteinic solution between 2 and 4, before being added to this solution.

It has also surprisingly been found that papain yields particularly interesting results for haemoglobins issued from animal species other than oxen, and naturally also for bovine cruor itself.

The moderate enzymatic hydrolysis to which the proteinic solution is subjected during the first step is used to prepare this solution at the second step of process. This second step has several aims. It allows first of all, to better fluidify the solution which has thickened while being acidified. It also allows to denaturize the enzyme introduced in the beginning of the reaction and to promote the agglutination of peptides or other substances bearing colored groups. Moreover, the whole process allows one, thanks to the acid pH and to high temperature, to reduce or destroy any bacterial contamination.

When the process applies to cruor, the latter, which generally contains 240-300 g hemoglobin per liter, is diluted with water, preferably by a factor of 4-6, so as to obtain a solution containing 40-75 g hemoglobin per liter. The solution is homogenized by shaking. The dilution triggers the lysis of red blood cells and the liberation of hemoglobin. The dilution is also necessary to prevent immediate coagulation of hemoglobin by acidification.

The solution is brought to a temperature of about 37° C., and an acid is added, preferably sulfuric acid, so as to adjust the pH between 2 and 4. The mixture thickens and its red color becomes brown. 50-150 mg pepsin, solubilized in the same acid, per liter of proteinic solution, are then added. The enzymatic hydrolysis is carried out at a temperature of about 37° C. during 10-30 minutes, without pH control. The latter increases by about 0.5 unit and stabilizes itself.

In a second step, the solution is then brought to a temperature above 60° C. and, preferably, not above 80° C. during 15 to 30 minutes, before centrifugation or filtration. A limpid pale yellow to light brown solution containing 80-90% of initial proteins is obtained.

The solution is then neutralized at a pH between 6 and 8, for example, with soda, which triggers the development of a dark precipitate, of negligible mass which is separated by centrifugation. A limpid slightly yellow colored liquid containing 40-50 g proteins per liter is then obtained.

When the enzyme used is papain the moderate enzymatic hydrolysis is carried out at a pH (usual for papain) between 5 and 8 and at a temperature (usual for papain) between 65 and 75° C., the second step being carried out at a temperature above 60° C., notably about 70° C., the pH being adjusted, preferably with sulfuric acid, at or below 5.

One may thus obtain more easily a decolorized juice with a single centrifugation. Moreover the slight pH variations allow one to limit as much as possible the generation of salts which must then be eliminated.

The salts generated by neutralization may easily be eliminated by ultrafiltration and the solution is concentrated.

The dehydration of this concentrated solution by freeze-drying or atomization gives a near white, odorless and insipid powder. This powder is made up of peptides of molecular mass 1,000-10,000 daltons.

In relation to prior processes, the inventive process has many advantages:

the dilution of cruor is weak and is essentially used for hemolysing the red blood cells to free hemoglobin;

no outside agent to be later recirculated or eliminated is introduced; this process requires neither organic solvents, nor adsorbants;

the reaction time is very short and the process may be carried out without any complicated apparatus, notably without a pH regulator;

the protein yield as well as decolorization are excellent; moreover, the obtained peptides are soluble whatever the pH;

the process is economical, being extremely simple to carry out and requiring no extreme pressures or temperatures.

EXAMPLE 1

The starting product is bovine blood cruor prepared in the slaughterhouse. Its hemoglobin concentration is 260 g/l. 25 ml cruor are added to 125 ml of demineralized water to the hemolysis of red blood cells and to obtain a 43.3 g hemoglobin per liter solution.

The solution is brought to 37° C. and pH is adjusted to 3 with a few drops of concentrated sulfuric acid.

25 mg T1000 pepsin according to CODEX 49 as a solution in 1 ml of 0.1N H.SO are added and the solution is kept at 37° C. by shaking during 15 minutes.

The mixture is then quickly brought to 80° C. and kept at that temperature by shaking during 20 minutes.

Ten minutes centrifugation at 9,000 rpm allow one to separate a 96 ml supernatant which is neutralized at pH 7 with NaOh. After standing for 2 hours at room temperature, another 10 minutes centrifugation allows one to discard a slight brown precipitate. The new obtained supernatant is light yellow, perfectly limpid and has a protein concentration of 44 g/l for a volume of 95 ml. The protein yield is therefore 80%.

EXAMPLE 2

300 ml bovine cruor diluted 6 times and containing 14 g hemoglobin are brought to 37° C. and pH is adjusted to 2 with concentrated sulfuric acid.

40 mg pepsin T1000 as a solution in 1 ml 0.1N H.SO are immediately introduced and the reaction takes place during 30 minutes. After this time, the pH has been stabilized at 2.6.

The solution is then brought to 80° C. during 30 minutes and then centrifugated during 15 minutes at 9,000 rpm.

The 228 ml limpid pale yellow supernatant which are collected contain 11.6 g proteins, which corresponds to a yield of 83%.

EXAMPLE 3

Bovine cruor is diluted so as to obtain a 50 g hemoglobin per liter solution 150 ml of this solution are treated at pH 2 and 37° C. during 30 minutes with 10 mg pepsin T1000, and are heated at 70° C. during again 30 minutes before being centrifugated 10 minutes at 9000 rpm.

The obtained clear and limpid supernatant is neutralized at pH 7 and left some time to stand at room temperature. The slight precipitate which has formed is eliminated by centrifugation. The 116 ml obtained product contain 6.4 g proteins.

By diafiltration followed by an ultrafiltration the solution is desalinated and concentrated, and then dried up by freeze-drying.

The obtained white powder is odorless and insipid. Its mass is 6.2 g and its analysis gives the following conclusions:

| | |
|---|---|
| moisture | 3.2% |
| residual mineral matter | 1.5% |
| peptide weight content | 5.9 g |

In polyacrylamide gel electrophoresis one can observe a neat band of apparent molecular mass 3500-4000 daltons.

EXAMPLE 4

50 l fresh bovine cruor corresponding to 14 kg hemoglobin are mixed with 250 l permutated water. 35 g pepsin T1000 as a solution in 3 l 0.1N H.SO are the added to the mixture and a pH is set to 2.1 with 27.5 l 1N H.SO.

The mixture is then brought to 37° C. and kept at that temperature during 30 minutes by shaking. At the end of the reaction the pH is stabilized at 2.4.

Finally, the mixture is brought to 75° C. and kept at that temperature during again half an hour.

After cooling to 44° C., the product is filtrated on a plate filter and 180 l filtrate are collected. The retention product is washed on the filter with 125 l of a 1.5 g/l NaCl solution, pH 2.5 with H.SO, and 150 l washing solution are collected and mixed with the first filtrate.

The thus obtained 330 l solution is neutralized at pH 7.2 with 11.15 l 2N NaOH.

After a night at +4° C., the mixture is centrifugated and the residue is discarded. The supernatant is desalinized by diafiltration and then concentrated by ultrafiltration.

The concentrate is then dried up by atomisation and 9 kg practically white globin derivative powder are obtained.

This powder may easily be put back in solution in water, whatever the starting pH.

EXAMPLE 5

100 g alfalfa are finely ground with 500 ml water with a household chopper. The obtained green soup is grossly filtrated on a Nylon cloth to eliminate the biggest fragments.

The suspension is adjusted to pH 2 with a few drops of sulfuric acid, then brought to 37° C. and 80 mg pepsin T1000 as a solution in 2 ml H.SO are added.

After 20 minutes reaction, the temperature is brought to 80° C. and kept at that level during 30 minutes.

By centrifugation at 9000 rpm during 15 minutes, 350 ml yellow supernatant containing 5 g proteins are obtained.

EXAMPLE 6

100 l bovine cruor containing 270 g hemoglobin per liter are diluted with 300 l permutated water, so as to obtain a 67.5 g/l solution with a pH of 7.2.

400 g papain sold under the denomination T400 and purified (proteolytic power according to CODEX 1949>400) as a solution in 2 l water are added and the mixture is homogeneized while stirring.

The temperature is then raised to 72° C. and kept at that level during 1 hour. After that, the pH has stabilized to 6.4 and 18 l 1N $H_2SO_4$ are introduced so as to adjust the pH to 5. Incubation is carried on during again 30 minutes at about 70° C.

The mixture is cleared up by filtrating on a rotatory filter.

After this step 430 l decolorized solution are obtained. The protein concentration is 47 g/l, which corresponds to a 75% yield

EXAMPLE 7

300 ml bovine cruor are added to 900 ml permutated water. The solution as obtained contains 55 g proteins per liter.

After 1.2 g purified T400 papain as a solution in 1 ml water are introduced the temperature is raised to 70° C. during 1 hour.

The pH is then adjusted to 5 with 56 ml 1N $H_2SO_4$ and the reaction is carried on during 30 minutes.

After centrifugating one obtains about 1 l decolorized supernatant which to be neutralized to pH 6.5 requires the addition of 21 ml 1N NaOH.

Analysis of this solution yields the following results:

| | |
|---|---|
| total nitrogen | 6.96 g/l |
| proteins (× 6.25) | 43.5 g/l |
| dry matter | 46.2 g/l |
| mineral matter | 3.7 g/l |

EXAMPLE 8

100 ml horse cruor representing 25 g hemoglobin are mixed with 300 ml permutated water.

Hydrolysis is carried out at 70° C. during 1 hour in the presence of 0.4 g purified T400 papain. The reaction proceeds during 30 minutes, the pH having been adjusted to 5 with a few drops concentrated $H_2SO_4$.

320 ml decolorized supernatant are then collected by centrifugation. The protein concentration is 62.8 g/l; the yield is thus above 80%.

EXAMPLE 9

520 ml whole sheep blood containing 169 g proteins/liter are added to 1 liter permutated water.

Hydrolysis is carried out during 1 hour at 70° C. in the presence of 4 g purified T400 papain.

The pH is then adjusted to 5 with 68 ml 1N $H_2SO_4$ and the reaction proceeds during 30 minutes at 70° C.

By centrifugation 1.4 l decolorized supernatant are collected. Neutralization of this solution at pH 6.5 requires 35 ml 1N NaOH.

Analysis of this solution yields the following results:

| | |
|---|---|
| total nitrogen | 7.1 g/l |
| proteins (× 6.5) | 44.4 g/l |
| dry matter | 50.7 g/l |
| mineral matter | 6 g/l |

What is claimed is:

1. A process for decolorizing a proteinic solution containing as pigment heminic or chlorophyll colored groups, comprising subjecting said proteinic solution to enzymatic hydrolysis to provide a partially hydrolyzed solution comprised of partially hydrolyzed protein and separated colored groups, adjusting the pH of said partially hydrolyzed solution to between 2 and 5 with sulfuric acid, and subjecting the resulting acidified solution to a temperature above 60° C. to improve the fluidity of the partially hydrolyzed solution and to trigger the agglutination of said colored groups.

2. A process according to claim 1, characterized in that pepsin at an acid pH between 2 and 4 is used as an enzyme during the hydrolysis step.

3. A process according to claim 2, characterized in that the pepsin used is pepsin T1000 in a proportion generally comprised between 0.1 and 0.5% in relation tot he mass of proteins in solution.

4. A process according to claim 1, characterized in that the enzyme is solubilized in sulfuric acid, before being added to the proteinic solution.

5. A process according to claim 1, characterized in that the enzymatic hydrolysis is carried during 10 to 30 minutes.

6. A process according to claim 1, characterized in that the acidified solution is brought to a temperature above 60° C. during 15 to 30 minutes.

7. A process according to claim 1, characterized in that the agglutinated colored groups are discarded and the resulting solution is neutralized at a pH between 6 and 8.

8. A process according to claim 1, characterized in that the neutralization is made with soda.

9. A process according to any of claims 7 and 8, characterized in that the salts generated by neutralization are eliminated by ultrafiltration, and that the solution is concentrated.

10. A process according to claim 1, characterized in that the proteinic solution which is subjected to hydrolysis is a hemoglobin solution obtained by hemolysis of cruor obtained from animal blood collected in the slaughterhouse.

11. A process according to claim 1, characterized in that the proteinic solution is a vegetal proteinic solution containing chlorophyll group.

12. A process according to claim 1, characterized in that when it is applied to the decolorization of cruor, the cruor is before hydrolysis diluted with water, preferably by a factor 4 to 6, so as to obtain a solution containing 40 to 75 g hemoglobin per liter, and that the solution is homogenized by shaking.

13. A process according to claim 9, characterized in that the proteins are collected in powder form by dehydration of the concentrated solution, by atomization or freeze-drying.

14. A process according to claim 1, wherein the enzyme used is papain, the enzymatic hydrolysis is carried out at a pH between 5-8 and at a temperature between 65-75° C., the partially hydrolyzed solution is brought to a temperature above 60° C. and adjusted with sulfuric acid to a pH at or below 5.

15. A process according to claim 14, characterized in that the partially hydrolyzed solution is brought to a temperature of about 70° C.

16. A process according to claim 14, characterized in that the proteinic solution which is treated is selected from the group consisting of bovine cruor, horse cruor and sheep cruor.

* * * * *

UNITED STATES PATENT AND TRADEMARK OFFICE
CERTIFICATE OF CORRECTION

PATENT NO. : 5,108,908
DATED : April 28, 1992
INVENTOR(S) : Jacques Coves; Jean-Louis Tayot It is certified that error appears in the above—identified patent and that said Letters Patent is hereby corrected as shown below:

In Column 5, line 26, delete "H.SO" and substitute therefor --$H_2SO_4$--.

In Column 5, line 32, delete "NaOh" and substitute therefor --NaOH--.

In Column 5, line 43, delete "H.SO" and substitute therefor --$H_2SO_4$--.

In Column 6, line 17, delete "H.SO" and substitute therefor --"$H_2SO_4$--.

In Column 6, line 28, delete "H.SO" and substitute therefor --"$H_2SO_4$--.

In Column 6, line 49, delete "H.SO" and substitute therefor --$H_2SO_4$--.

Signed and Sealed this

Seventh Day of September, 1993

Attest:

BRUCE LEHMAN

*Attesting Officer*      *Commissioner of Patents and Trademarks*